United States Patent [19]

Yates

[11] Patent Number: 4,940,824

[45] Date of Patent: Jul. 10, 1990

[54] PROCESS FOR REMOVING VINYLIDENE CHLORIDE FROM 1,1-DICHLORO-1-FLUOROETHANE

[75] Inventor: Stephen F. Yates, Arlington Hts., Ill.

[73] Assignee: Allied-Signal Inc., Morris Township, Morris County, N.J.

[21] Appl. No.: 450,654

[22] Filed: Dec. 14, 1989

[51] Int. Cl.⁵ .............................................. C07C 17/38
[52] U.S. Cl. ..................................................... 570/179
[58] Field of Search ......................................... 570/179

[56] References Cited

U.S. PATENT DOCUMENTS

| | | | |
|---|---|---|---|
| 2,894,044 | 7/1959 | Prill | 260/653.7 |
| 3,833,676 | 9/1974 | Ukaji et al. | 260/653.7 |
| 4,820,681 | 4/1989 | Chang et al. | 502/418 |
| 4,849,558 | 7/1989 | Goodman | 570/179 |

FOREIGN PATENT DOCUMENTS

| | | | |
|---|---|---|---|
| 1040436 | 2/1989 | Japan | 570/179 |
| 846677 | 8/1960 | United Kingdom | 570/179 |

OTHER PUBLICATIONS

Jüntgen et al., Fuel, 1981, vol. 60, Sep., pp. 817–822.
Chihara et al., Journal of Colloid and Interface Science, vol. 64, No. 3, May 1978, pp. 584–587.

Primary Examiner—Alan Siegel
Attorney, Agent, or Firm—Harold N. Wells; Jay P. Friedenson; Gerard P. Rooney

[57] ABSTRACT

Vinylidene chloride can be substantially removed from a stream of CFC-141b over a carbon molecular sieve having a mean pore size of about 4.2 to 4.5 Angstroms.

4 Claims, 1 Drawing Sheet

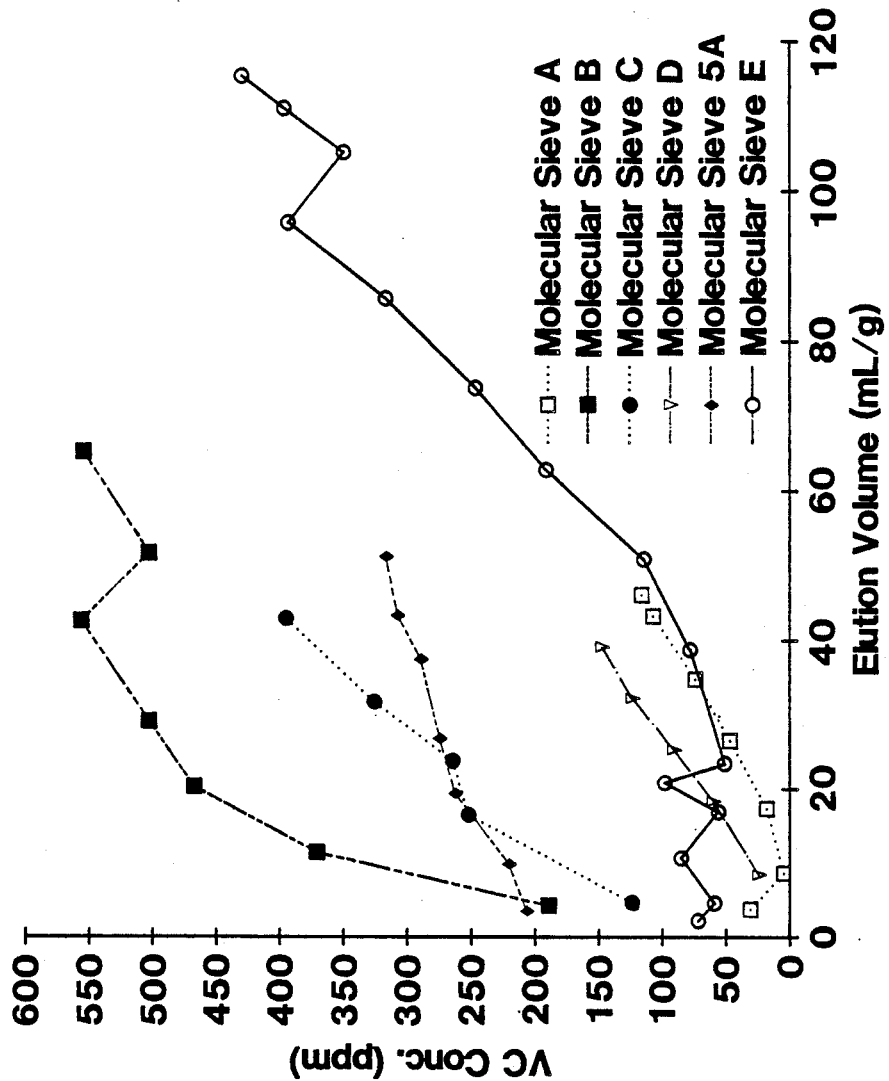

PROCESS FOR REMOVING VINYLIDENE CHLORIDE FROM 1,1-DICHLORO-1-FLUOROETHANE

PRIOR ART

This invention relates to the purification of 1,1-dichloro-1-fluoroethane, also designated CFC-141b, which has been of particular interest as a replacement for chlorofluorocarbons having similar physical properties, particularly CFC-11, -12, and -113. CFC-141b may be prepared by reaction of vinylidene chloride or trichloroethane with HF. Such processes are disclosed, for example, in U.S. Pat. Nos. 2,894,044 and 3,833,676.

It is characteristic of such reactions that many by-products are formed, containing varying numbers of hydrogen, chlorine, and fluorine atoms on methane, ethane, and ethylene molecules. These by-products and the unreacted feed material may be separated by distillation where possible. Other compounds are relatively harmless since their presence does not greatly alter the physical properties for which CFC-141b is useful. Vinylidene chloride has a boiling point close to that of CFC-141b making it difficult to separate them by distillation.

Further improvement in methods of purifying CFC-141b, particularly with respect to removing unreacted vinylidene chloride is desired and the present inventor has discovered a means for purification by adsorption which will be disclosed in detail below.

SUMMARY OF INVENTION

Vinylidene chloride may be present in the impure CFC-141b at concentrations of about 200 to 900 ppm by weight, depending upon the degree of conversion to CFC-141b and any previous separation steps. Up to about 95% of the vinylidene chloride can be removed by the invention, leaving about 50 to 200 wt.ppm in the CFC-141b.

The CFC-141b stream is passed over a carbon molecular sieve having a mean pore size between about 4.2 to 4.5 Angstroms at a temperature of about $-20°$ C. to $60°$ C. and a pressure of about 100 to 500 kPa. With respect to most of the other impurities expected to be present in the CFC-141b stream, such molecular sieves have little or no capacity, making the removal of vinylidene chloride highly selective.

The process may be carried out with CFC-141b in the liquid or vapor phase. Where a fixed bed of zeolite particles is used, CFC-141b vapor may be passed over the particles with a gas hourly space velocity of about 130 to 1500 $hr^{-1}$. The corresponding liquid space velocity for liquid phase operation would be about 1 to 15 $hr^{-1}$.

BRIEF DESCRIPTION OF THE DRAWINGS

The sole FIGURE is a graph showing adsorption of vinylidene chloride on various carbon molecular sieves.

DESCRIPTION OF THE PREFERRED EMBODIMENTS

Absorption of Vinylidene Chloride

Vinylidene chloride is present in CFC-141b in amounts between about 200 and 900 wt.ppm depending upon the conversion to CFC-141b and preliminary purification steps.

It is preferred that unreacted vinylidene chloride be removed selectively from CFC-141b. Distillation is commonly used, but where the boiling points are close, the separation is difficult and expensive. Vinylidene chloride and CFC-141b fall in that category. Adsorption may be considered for such separations. However, an adsorbent may remove more than the target compound, i.e. vinylidene chloride, and thus the cost of removing it increases. Also, when the adsorbent is regenerated the target compound will be contaminated with other compounds. However, the present inventor has found that by selecting the proper molecular sieve adsorbent vinylidene chloride can be separated from CFC-141b and recycled to the fluorination process.

As will be seen in the examples below, vinylidene chloride is not removed to a significant extent by many molecular sieve materials, including silicalite, CaX, CaY, and calcium chabazite (AW-500). However, carbon molecular sieves having a pore size of about 4.2 Å to 4.5 Å provide an effective and selective means for separating vinylidene chloride from CFC-141b.

Carbon Molecular Sieves

Carbon molecular sieves are available commercially. They are usually derived from natural sources such as coal. One example is the carbon molecular sieves described in a paper by Juntgen et al. of Bergbau-Forschung GmbH in *FUEL*, 1981, Vol. 60, September, p. 817–822.

Another carbon molecular sieve which may be used for the purification of fluorocarbons is produced by a unique method disclosed in U.S. Pat. No. 4,820,681 and incorporated herein by reference. This method of manufacturing may be broadly characterized as comprising three steps: (1) polymerization of an oxygen-free monomer in the presence of an oxygen-free cross-linking agent; (2) forming particles of the resultant polymer into a desired shape; and then, (3) carbonizing the shaped material in a substantially oxygen-free environment.

The monomer can be chosen from a number of different monomers. They should be readily polymerizable, essentially free of oxygen in their molecular structure and preferably comprised basically of hydrogen, a halogen, and carbon. Among the materials which may be employed as the monomer are acrylonitrile (AN), vinylidene fluoride (PVDF), chlorotrifluoroethylene (HALAR), vinylidene chloride (PVDC), mixtures of two or more monomers such as mixtures of vinylidene chloride and vinyl chloride, vinylidene chloride and acrylonitrile, and a mixture of styrene and divinylbenzene. Other suitable monomers are vinyl fluoride, vinyl bromide, chlorinated ethylene, chlorofluorethylene, vinyl chlorobenzene, vinylidene bromide and vinylidenefluoridechlorotrifluoroethylene. The preferred monomer is vinylidene chloride. Polymerization reactions may be performed according to a number of different procedures known in the art. However, the most favorable results have been obtained employing a bulk polymerization or a solution polymerization.

The polymers produced in the initial polymerization step should be cross-linked with a substantially oxygen-free cross-linking agent. The cross-linking agent will typically be present during the polymerization at a concentration equal to less than 10 mole percent of the monomer. A preferred cross-linking agent is divinylbenzene. Other possible cross-linking agents include trivinyl benzene, divinyl acetylene, and divinyl sulfide.

As the production of carbon molecular sieves from polymers having a no-oxygen functionality is desired, the polymerization initiator is also preferably an oxygen-free compound. Therefore, a carbon or azo rather than an oxygen initiator is preferably used.

The polymeric material is carbonized by heating to a high temperature in an essentially oxygen-free environment. Prior to high temperature carbonization the polymer precursor material is subjected to a mild heating step during which its temperature is raised above 150° C., e.g. 240° C., and held at this temperature until no more weight loss occurs. The material is then preferably subjected to a programmed temperature increase to a temperature above 700° C., preferably above 800° C., particularly, above 900° C. Sieve precursors derived from polymeric materials are substantially free of the inorganic materials such as metals and inorganic oxides which may be present when the precursor material is made from a naturally occurring substance such as coal, coconut shells, peat, or wood. The preferred sieves, on a hydrogen- and oxygen-free basis, should contain at least 99.5 wt. % carbon and preferably at least 99.8 wt. % carbon.

While the just described method produces a unique and useful carbon molecular sieve, the average pore size is believed to be slightly above 3.8 Angstroms and accordingly, it must be further treated to increase the pore size to meet the needed size range. Various techniques may be used to increase the pore size, such as treatment with steam at temperatures between about 700° C. and 1000° C., treatment with air at temperatures between about 400° C. and 600° C., or treatment with $CO_2$ at temperatures between about 700° C. and 1000° C.

It should be noted that determination of the pore size of carbon molecular sieves is difficult and consequently, accurate values are not always available. Several approaches have been used. In the first method, a series of molecules of increasing size are brought in contact with the carbon molecular sieve and the amount adsorbed measured in a McBain balance. When amount of a molecule adsorbed is substantially greater than found with other molecules, the pore size is considered to have been determined. In the second method, a mixture of gases of known molecular size and similar structure is tested for their behavior when a carbon molecular sieve is used as a chromatographic adsorbent. The pore size is estimated by observing which of these gases is retained on the adsorbent. Yet another method requires the measurement of the isosteric heat of adsorption of a gas or gases. The pore size is given by the intersection of a line drawn at this energy with the Lennard-Jones potential curve for that gas. An example of this last technique is given by K. Chihara et al. in the *Journal of Colloid and Interface Science,* 64, 584 (1978), in which the pore size of molecular sieve MSC-5A was found to be 4.4 Å.

Process

When CFC-141b is produced by catalytic hydrofluorination of vinylidene chloride conversion to CFC-141b will be only partial and many by-products will be produced. Consequently, the reactor effluent will be separated by distillation to concentrate the CFC-141b product and to produce a recycle stream of unreacted feed. The resulting impure CFC-141b stream will contain unreacted HF and vinylidene chloride, and minor amounts of various by-product impurities. The HF and HCl can be removed selectively by a technique disclosed by others and not part of the present invention. Once done, the CFC-141b will still contain impurities which should be removed, including about 200 to 900 wt.ppm of vinylidene chloride. The present process is intended to remove vinylidene chloride down to below 200 wt.ppm in CFC-141b, preferably below 50 wt.ppm.

The CFC-141b feed stream could be either in the liquid or gas phase, although the liquid phase would be preferred to avoid the costs of vaporizing and later condensing the feed stream. Various techniques known to those skilled in the art could be used for contacting the CFC-141b stream with the carbon molecular sieve adsorbent, such as fluidized or moving beds, but typically a packed bed of adsorbent particles would be used. Selection of the particle size, bed shape, and the space velocity of the CFC-141b stream would be determined according to known principles as required to provide the desired removal of dichloroacetylene. Generally, the gas hourly space velocity of the CFC-141b stream would be about 130 to 1500 $hr^{-1}$ when operating with a vapor feed. The corresponding liquid space velocity would be about 1 to 15 $hr^{-1}$. Adsorption would be carried out at a suitable temperature, generally between about $-20°$ C. to 60° C. and a pressure dependent upon whether liquid or vapor contacting is desired, between about 100 to 500 kPa.

The adsorbent bed should provide an optimum capacity for vinylidene chloride, balancing the costs for equipment and adsorbent versus the costs of regeneration. When the useful capacity has been reached, the adsorbent will be regenerated by heating the bed with a gas stream to remove the vinylidene chloride. The CFC-141b remaining in the vessel and on the adsorbent will be removed first and recovered and then the regeneration process will be carried out. After the bed has been fully heated and the vinylidene chloride removed, it will be cooled and reintroduced to service. The conditions needed to optimally regenerate the adsorbent will be determined by the adsorbent used and the available utilities. Typically, it would be expected that heating the bed of adsorbent to about 200° C. to 500° C. with a stream of nitrogen would provide satisfactory regeneration.

EXAMPLE 1

A number of potential adsorbents were tested for their ability to remove vinylidene chloride. A sample of 15 mL of impure CFC-141b containing 576 wt.ppm vinylidene chloride, 16 wt.ppm of dichloroacetylene, 840 wt.ppm CFC-142b (1-chloro-1,1-difluoroethane), and 20 wt.ppm CFC-1131a (1-chloro-1-fluoroethylene) was placed in a 20 mL vial with 1.0 gm of the adsorbent to be tested. After agitating for 1 hour, a sample of the liquid was removed and analyzed by gas chromatography using two 3.175 mm diameter stainless steel columns in series (6.1 m of n-octane-Porasil C and 2 m of 10% OV-101 on Chromosorb W, both materials 80/100 mesh from Alltech Associates) and 18 mL/min of nitrogen as a carrier gas. The results are given in the Table below.

TABLE 1

| Adsorbent | Vinylidene Chloride wt. ppm |
|---|---|
| Feed (no adsorbent) | 576 |
| Chabazite (AW-500)[a] | 1340 |
| 5A[b] | 455 |
| 3A[c] | 608 |
| Calcium X[d] | 660 |
| Mordenite (AW-300)[e] | 1760 |
| Carbon Mol. Sieve[f] | 301 |
| Carbon Mol. Sieve[g] | 75 |

TABLE 1-continued

| Adsorbent | Vinylidene Chloride wt. ppm |
|---|---|
| Carbon Mol. Sieve[h] | 275 |
| Carbon Mol. Sieve[i] | 213 |

[a] Supplied by UOP
[b] Supplied by UOP
[c] Supplied by UOP
[d] Supplied by UOP
[e] Supplied by UOP
[f] Prepared by procedure of U.S. Pat. No. 4,820,681 using polyvinylidene chloride carbonized at 800° C.
[g] Supplied by Takeda Chemical Co. (MSC-5A)
[h] Supplied by Bergbau-Forschung GmbH
[i] Supplied by Bergbau-Forschung GmbH and then steamed at 850° C. for 30 minutes
Essentially none of the CFC-142b and CFC-1131a were removed.

It can be seen that most of the adsorbents did not remove vinylidene chloride very well. In fact, the amount of vinylidene chloride appeared to increase in some instances, which is attributed to defluorination of CFC-141b. The carbon molecular sieves all adsorbed vinylidene chloride and the differences in performance are attributed to differences in pore size. Carbon molecular sieve (f) is believed to have a pore size slightly larger than 3.8 Å and was less effective than carbon molecular sieve (g) which has been reported to have a pore size of 4.4 Å. Carbon molecular sieve (h) is believed to have an intermediate pore size and gave intermediate results, but when steam treated to open the pores (i) the capacity for vinylidene chloride increased.

EXAMPLE 2

In addition to the static screening experiments described in Example 1, tests were carried out in which impure CFC-141b containing 400 wt.ppm vinylidene chloride, 840 wt.ppm CFC-142b and 20 wt.ppm CFC-1131a was pumped at 0.88 mL/min through a 9.5 mm diameter column 177.8 mm long containing 5-10 g of the absorbent to be tested (crushed to 20-50 mesh). The rate was fixed by pumping the feed through 6 meters of 0.0254 mm stainless steel capillary tubing with the pressure at the outlet maintained at 272 kPa gauge. A sample of the CFC-141b leaving the adsorbent column was obtained after 15-30 minutes and analyzed by gas chromatography in the apparatus described in Example 1.

TABLE 2

| Absorbent | CFC-142b (ppm) | CFC-1131a (ppm) | Vinylidene Chloride (ppm) |
|---|---|---|---|
| Feed (no adsorbent) | 840 | 20 | 400 |
| AW-500[a] | 870 | 20 | 680 |
| Silicalite[b] | 780 | 20 | 390 |
| Calcium X[c] | 830 | 30 | 420 |
| Calcium Y[d] | 900 | 20 | 380 |
| 5A[e] | 750 | 15 | 220 |
| Carbon Mol. Sieve[f] | 654 | 14 | 31 |
| Carbon Mol. Sieve[g] | 428* | 9 | 189 |

[a] Chabazite, supplied by UOP
[b] Supplied by UOP
[c] Supplied by UOP
[d] Supplied by UOP
[e] Supplied by UOP
[f] Supplied by Takeda Chemical Co.
[g] Prepared by procedure of U.S. Pat. No. 4,820,681 using polyvinylidene chloride carbonized at 800° C.
*Feed concentration 453 ppm Note that most of the zeolites either showed no affinity for vinylidene chloride or resulted in a net increase in vinylidene chloride concentration. We attribute the increases, where present, to defluorination of CFC-141b as previously mentioned. The best adsorbents were the carbon molecular sieves. Comparison of carbon molecular sieves (f) and (g) shows the importance of correct pore size. Sieve (f) has a pore size of 4.4 Å, while (g) has a pore size somewhat larger than 3.8 Å.

EXAMPLE 3

Several carbon molecular sieves were tested using the procedure described in Example 2 except that a series of CFC-141b samples were analyzed to determine the capacity of the carbon molecular sieves. The results of analyses for vinylidene chloride during each run are shown in the FIGURE, plotted vs. the volume of CFC-141b eluted divided by the weight of adsorbent used. Capacities were calculated from each curve by noting the point at which the curve crossed a line drawn at one half the feed concentration, and assuming that all of the vinylidene chloride up to that point was adsorbed.

TABLE 3

| Molecular Sieve | Capacity (mg/g) | Source |
|---|---|---|
| A | 49.0 | Takeda Chemical Co. (HGR-805) |
| B | 3.34 | Prepared by procedure of U.S. Pat. No. 4,820,681 using polyvinylidene chloride carbonized at 800° C. |
| C | 8.62 | Bergbau-Forschung |
| D | 28.0 | Prepared by steam treatment at 850° C. of carbon from Bergbau-Forschung |
| E | 33.4 | Takeda Chemical Co. (MSC-5A) |

I claim:
1. A process for purifying 1,1-dichloro-1-fluoroethane (CFC-141b) containing about 200 to 900 wt.ppm vinylidene chloride comprising passing said 1,1-dichloro-1-fluoroethane over a carbon molecular sieve having a mean pore size between about 4.2 to 4.5 Angstroms at a temperature of −20° C. to 60° C. and a pressure of about 100 to 500 kPa and recovering 1,1-dichloro-1-fluoroethane containing less than 200 wt.ppm of vinylidene chloride.

2. The process of claim 1 wherein said carbon molecular sieve is a fixed bed of particles, the 1,1-dichloro-1fluoroethane is a gas, and the gas hourly space velocity of said 1,1-dichloro-1-fluoroethane is about 130 to 1500 $hr^{-1}$.

3. The process of claim 1 wherein said carbon molecular sieve is a fixed bed of particles, the 1,1-dichloro-1fluoroethane is a liquid, and the liquid hourly space velocity of said 1,1-dichloro-1-fluoroethane is about 1 to 15 $hr^{-1}$.

4. The process of claim 1 wherein the recovered 1,1-dichloro-1-fluoroethane contains less than 50 wt. ppm of vinylidene chloride.

* * * * *